US010107930B2

(12) United States Patent
Li et al.

(10) Patent No.: US 10,107,930 B2
(45) Date of Patent: Oct. 23, 2018

(54) HYBRID SATURATION RECOVERY-INVERSION RECOVERY PULSE SEQUENCE FOR IMPROVED NMR LOGGING OF BOREHOLES

(71) Applicant: HALLIBURTON ENERGY SERVICES, INC., Houston, TX (US)

(72) Inventors: Lilong Li, Humble, TX (US); Songhua Chen, Katy, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 740 days.

(21) Appl. No.: 14/401,097

(22) PCT Filed: May 16, 2013

(86) PCT No.: PCT/US2013/041337
§ 371 (c)(1),
(2) Date: Nov. 13, 2014

(87) PCT Pub. No.: WO2013/173575
PCT Pub. Date: Nov. 21, 2013

(65) Prior Publication Data
US 2015/0145513 A1    May 28, 2015

Related U.S. Application Data

(60) Provisional application No. 61/647,671, filed on May 16, 2012.

(51) Int. Cl.
*G01V 3/32* (2006.01)
*G01N 27/08* (2006.01)
(Continued)

(52) U.S. Cl.
CPC .............. *G01V 3/32* (2013.01); *E21B 47/12* (2013.01); *G01N 24/081* (2013.01); *G01R 33/448* (2013.01)

(58) Field of Classification Search
CPC ........ G01V 3/32; E21B 47/12; G01N 24/081; G01R 33/448
See application file for complete search history.

(56) References Cited

U.S. PATENT DOCUMENTS

| 4,694,250 A | 9/1987 | Iwaoka et al. |
| 5,023,551 A | 6/1991 | Kleinberg et al. |

(Continued)

FOREIGN PATENT DOCUMENTS

WO   WO-2013/173575   11/2013

OTHER PUBLICATIONS

AU Patent Examination Report No. 1, dated May 8, 2015, Appl No. 2013/262770, "Hybrid Saturation Recovery-Inversion Recovery Pulse Sequence for Improved NMR Logging of Boreholes," Filed May 16, 2013, 3 pgs.

(Continued)

*Primary Examiner* — Gregory H Curran
(74) *Attorney, Agent, or Firm* — Gilliam IP PLLC

(57) ABSTRACT

A nuclear magnetic resonance (NMR) logging method includes providing a hybrid pulse sequence having a saturation pulse, an inversion pulse, and a detection sequence. The method also includes measuring echo signals in response to the hybrid pulse sequence. The method also includes deriving a spin-lattice time constant ($T_1$) distribution from the measured echo signals. A NMR system includes a hybrid pulse sequence module to provide a hybrid pulse sequence with a saturation pulse, an inversion pulse, and a detection sequence. The NMR system also includes a control module to select a time interval between the saturation pulse and the inversion pulse.

22 Claims, 14 Drawing Sheets

(51) Int. Cl.
  *G01R 33/44* (2006.01)
  *E21B 47/12* (2012.01)
  *G01N 24/08* (2006.01)

(56) References Cited

U.S. PATENT DOCUMENTS

| | | | |
|---|---|---|---|
| 5,486,762 | A | 1/1996 | Freedman et al. |
| 6,392,409 | B1 | 5/2002 | Chen |
| 6,492,809 | B1 | 12/2002 | Speier et al. |
| 6,531,868 | B2 | 3/2003 | Prammer |
| 6,600,316 | B2 | 7/2003 | Chen et al. |
| 6,844,728 | B2 | 1/2005 | Speier et al. |
| 6,897,652 | B2 | 5/2005 | Appel et al. |
| 6,937,014 | B2 | 8/2005 | Sun et al. |
| 6,987,385 | B2 | 1/2006 | Akkurt et al. |
| 7,358,725 | B2 | 4/2008 | Blanz |
| 7,808,238 | B2 | 10/2010 | Chen |
| 8,400,147 | B2 * | 3/2013 | Anand .......... G01N 24/081 324/303 |
| 2003/0006766 | A1 | 1/2003 | Kruspe et al. |
| 2004/0027122 | A1 | 2/2004 | Heaton et al. |
| 2004/0041562 | A1 | 3/2004 | Speier |
| 2005/0030021 | A1 | 2/2005 | Prammer et al. |
| 2005/0104587 | A1 | 5/2005 | Akkurt |
| 2007/0241750 | A1 | 10/2007 | Akkurt |
| 2010/0134104 | A1 | 6/2010 | Song et al. |
| 2011/0074417 | A1 | 3/2011 | Kitane et al. |

OTHER PUBLICATIONS

O'Donnell M. et al, "Toward an automated analysis system for nuclear for nuclear magnetic resonance imaging. I. Efficient pulse sequences for simultaneous T1-T2 Imaging," Medical Physics AIP. Melville, NY, US. vol. 13. No. 2. Mar. 1, 1986 (Mar. 1, 1986). pp. 182-190.

Li L et al: "Sensitive new NMR hybrid T1 1-14 measurements for gas shale. heavy oil. and microporosity characterization," XP-002746374, SPE 158833, Proceedings—SPE Annual Technical Conference and Exhibition held in San Antonio, TX, USA, Oct. 8-10, 2012.

EP Extended Search Report, dated Oct. 28, 2015, Appl. No. 13791510.4, "Hybrid Saturation Recovery-Inversion Recovery Pulse Sequence for Improved NMR Logging of Boreholes," filed May 16, 2013, 7 pgs.

GCC Second Examination Report, dated Jul. 20, 2016, Appl No. 24418, "Hybrid Saturation Recovery-Inversion Recovery Pulse Sequence for Improved NMR Logging of Boreholes," Filed May 18, 2013, 6 pgs.

Hardy, C. J. et al., "Calculated T1 Images Derived from a Partial Saturation-Inversion Recovery Pulse Sequence with Adiabatic Fast Passage", Magnetic Resonance Imaging, 1985, p. 107-116, vol. 3, No. 2, Pergamon Press Ltd., USA.

Fram, Evan K. et al., "Rapid Calculation of T1 Using Variable Flip Angle Gradient Refocused Imaging", Magnetic Resonance Imaging, vol. 5, pp. 201-208, 1987, 8 pgs.

Mehta, Rahul C. et al., "MR Evaluation of Vertebral Metastases: T1-weighted, Short-Inversion-Time Inversion Recovery, Fast Spin-Echo, and Inversion-Recovery Fast Spin-Echo Sequences", AJNR Am J Neuroradiol 16: American Society of Neuroradiology, Feb. 1995, pp. 281-288.

Kim, Raymond J. et al., "How We Perform Delayed Enhancement Imaging", Journal of Cardiovascular Magnetic Resonance, 2003, p. 505-514, vol. 5, No. 3, pp. 505-514, Marcel Dekker, Inc., New York, NY 10016.

Chen, Songhua et al., "A New NMR T1 Measurement Technique for Gas Shale, Heavy Oil, and Microporosity Characterizations", the International Symposium of the Society of Core Analysts held in Aberdeen, Scotland, UK; SCA2012-Paper #A033; Aug. 27-30, 2012; 12 pgs.

PCT International Search Report and Written Opinion, dated Oct. 2, 2013, Application No. PCT/US2013/041337, "Hybrid Saturation Recovery-Inversion Recovery Pulse Sequence for Improved NMR Logging of Boreholes", filed May 16, 2013, 13 pgs.

PCT International Preliminary Report on Patentability, dated May 16, 2014, Application No. PCT/US2013/041337, "Hybrid Saturation Recovery-Inversion Recovery Pulse Sequence for Improved NMR Logging of Boreholes", filed May 16, 2013, 17 pgs.

* cited by examiner

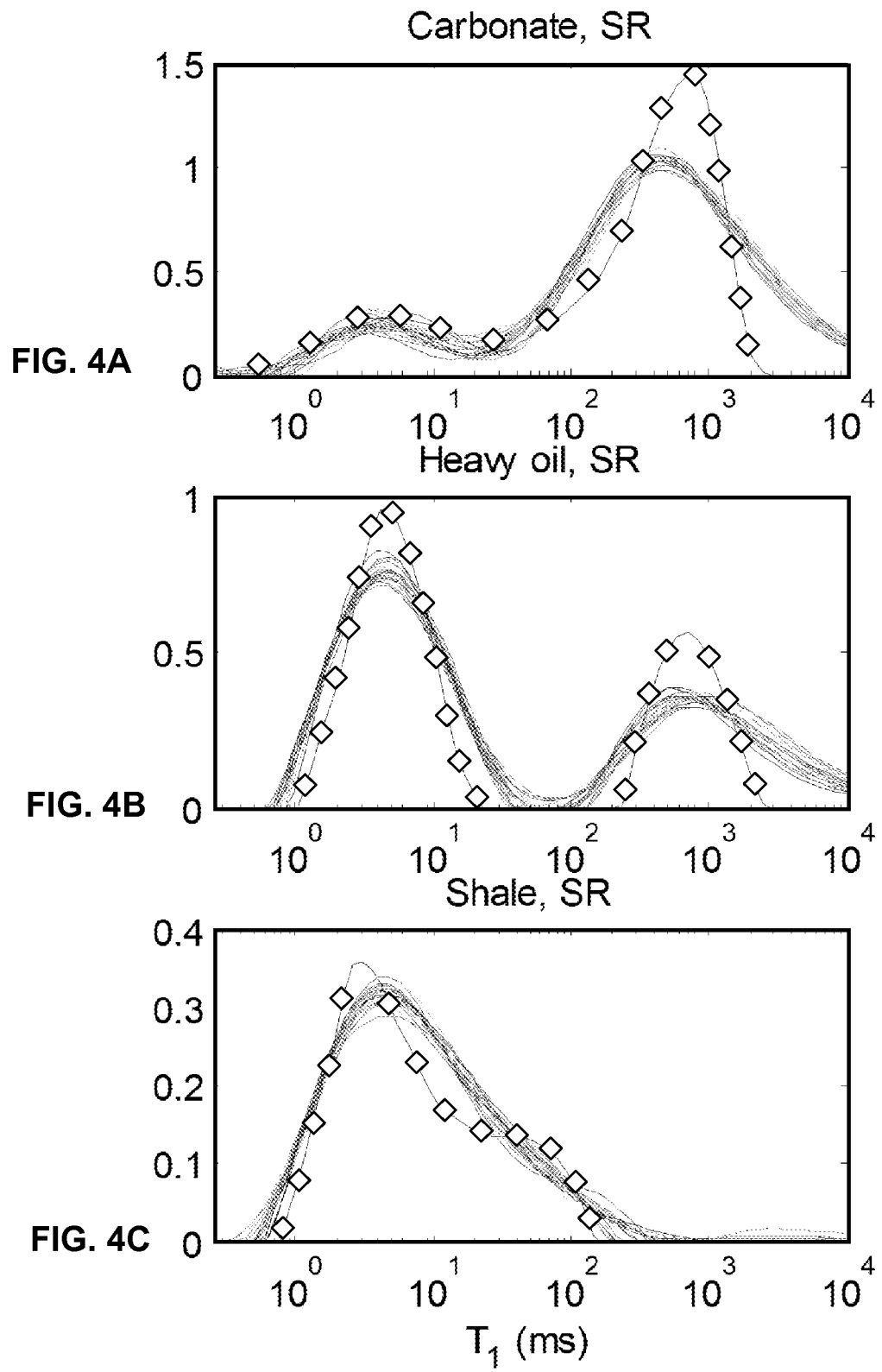

HYBRID SATURATION RECOVERY-INVERSION RECOVERY PULSE SEQUENCE FOR IMPROVED NMR LOGGING OF BOREHOLES

CROSS-REFERENCE TO RELATED APPLICATIONS

This application claims priority to Provisional U.S. Application Ser. No. 61/647,671, entitled "Hybrid Saturation Recovery-Inversion Recovery Pulse Sequence for Improved NMR Logging of Boreholes" filed May 16, 2012 by Lilong Li and Songhua Chen, which is hereby incorporated herein by reference.

BACKGROUND

Understanding the structure and properties of geological formations can improve the efficiency of oil field operations such as drilling, well completion, and production. The collection of information relating to conditions downhole, commonly referred to as "logging," can be performed by several methods including nuclear magnetic resonance (NMR) logging.

NMR logging tools operate by using an imposed static magnetic field, $B_0$, to give nuclei with non-zero nuclear spin (non-zero magnetic moment and angular momentum) split energy levels. Since lower energy levels are preferred, an ensemble of nuclei will exhibit an anisotropic distribution of energy states, giving the nuclear spins a preferential polarization parallel to the imposed field. This state creates a net magnetic moment and produces a bulk magnetization. The nuclei converge upon their equilibrium alignment with a characteristic exponential relaxation time constant. When this convergence occurs after the nuclei have been placed in a cooperative initial state (discussed below), it is known as recovery. The time constant for recovery is called the "spin-lattice" or "longitudinal" relaxation time ($T_1$).

During or after the polarization period, the tool applies a perturbing field, usually in the form of a radio frequency electromagnetic pulse whose magnetic component ($B_1$) is perpendicular to the static field ($B_0$). This perturbing field moves the orientation of the magnetization into the transverse (perpendicular) plane. The frequency of the pulse can be chosen to target specific nuclei (e.g., hydrogen). The polarized nuclei are perturbed simultaneously and, when the perturbation ends, they precess around the static magnetic field gradually re-polarizing to align with the static field once again while losing coherence in the transverse plane ($T_2$ relaxation). The precessing nuclei generate a detectable radio frequency signal that can be used to measure statistical distributions of $T_1$, $T_2$, porosities, and/or diffusion constants. To recover NMR measurements, data sampling is performed during a pulse sequence that generates free-induction decay or spin echoes. The data sampling process is limited by timing constraints of the receiver electronics as well as timing criteria of the NMR experiment.

For NMR-based formation evaluation, $T_1$ measurements are sometimes preferred over $T_2$ measurements because they may be less vulnerable to vibrations. Further, interpreting $T_1$ data may be simpler than interpreting $T_2$ data because $T_1$ data is not affected by the additional signal decay caused by the molecular diffusion in the magnetic field gradients. Moreover, $T_1/T_2$ data provide additional formation and fluid information than $T_2$ data alone. Despite these benefits, $T_1$ measurements may suffer from either very long measurement time using the inversion-recovery (IR) data acquisition method, or reduced sensitivity in the short relaxation time range using the saturation-recovery (SR) method.

BRIEF DESCRIPTION OF THE DRAWINGS

Accordingly, there are disclosed herein various methods and systems nuclear magnetic resonance (NMR) analysis using a hybrid pulse sequence to improve $T_1$ measurements.

FIGS. 4A-4F show illustrative high signal-to-noise ratio (SNR) inversion results.

Figure 1:
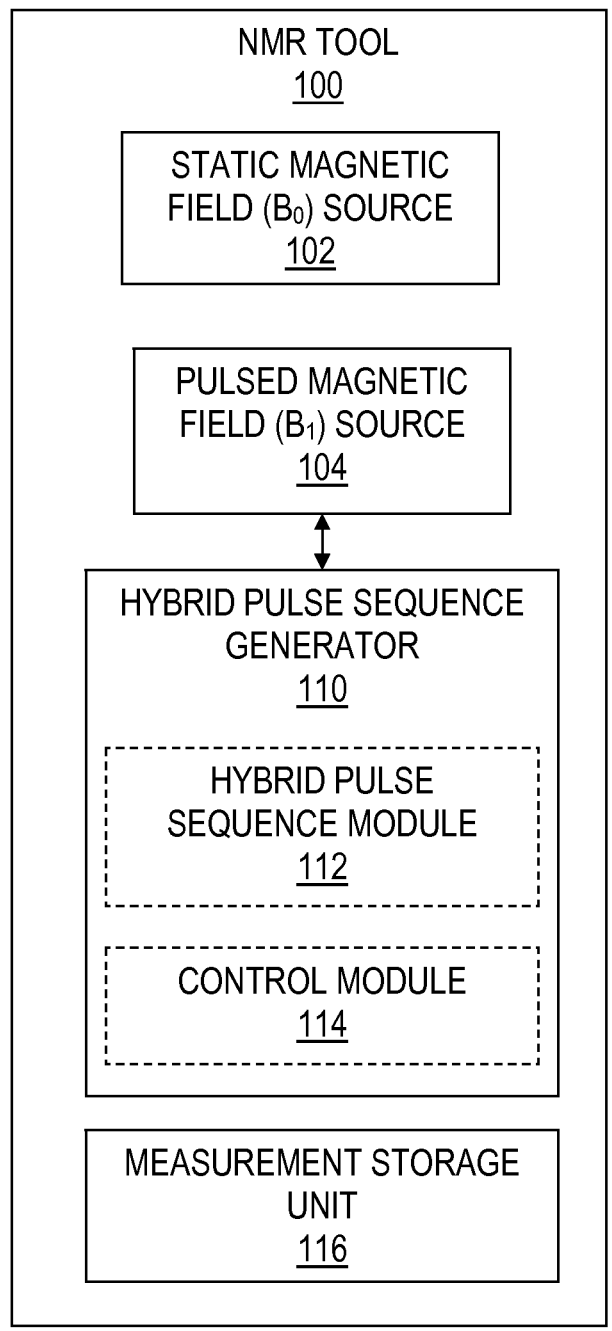
FIG. 1 is a block diagram of an illustrative NMR tool.

It should be understood, however, that the specific embodiments given in the drawings and detailed description below do not limit the disclosure. On the contrary, they provide the foundation for one of ordinary skill to discern the alternative forms, equivalents, and other modifications that are encompassed in the scope of the appended claims.

DESCRIPTION

Disclosed herein are methods and systems for nuclear magnetic resonance (NMR) analysis using a hybrid pulse sequence that combines saturation-recovery (SR) and inversion-recovery (IR). Data acquisition using the hybrid pulse sequence retains the efficiency of SR while securing increased sensitivity characteristics of IR, thereby improving the performance of NMR analysis for fast relaxing components abundant in gas shale, heavy oil, and for microporosity in carbonates.

As an example application, an NMR logging tool using the hybrid pulse sequence may measure the distribution of lattice relaxation time ($T_1$) in a sample, where various $T_1$ times may be present. Such distributions are helpful for downhole formation evaluation because different types of fluids reside in pores of different sizes. Thus, the combined fluids produce vastly different $T_1$ values in NMR measurements. With the disclosed hybrid pulse sequence, the NMR logging tool sensitivity to fast-relaxing $T_1$ components (components with very small $T_1$) is improved without significantly extending the measurement time.

FIG. 1 is a block diagram of an illustrative NMR tool 100. In some embodiments, the NMR tool 100 is part of a downhole wireline logging string or a logging-while-drilling (LWD) string to analyze formation attributes. In another embodiment, the NMR tool 100 corresponds to laboratory equipment to analyze samples. As shown, the NMR logging tool 100 includes a static magnetic field ($B_0$) source 102, such as one or more strong, permanent magnets (e.g., samarium cobalt magnets). The NMR logging tool 100 also includes a pulsed magnetic field ($B_1$) source 104 to emit pulses of an alternating radio frequency (RF) magnetic field using one or more antennas with suitable electronics. Note that such antennas and electronics can act in a dual role, also functioning to receive and detect spin echo signals. Alternatively such receiving can be done with separate antennas and electronics.

The NMR logging tool 100 further includes a hybrid pulse sequence generator 110 in communication with the pulsed magnetic field source 104. In some embodiments, the hybrid pulse sequence generator 110 includes a processor and a memory with executable software instructions. In alternative embodiments, the hybrid pulse sequence generator 110 corresponds to hardware modules such as programmable logic or application-specific integrated circuits (ASICs) configured to provide any of the hybrid pulse sequence variations described herein. The hybrid pulse sequence generator 110 directs the pulsed magnetic field source 104 to output a particular pulse sequence and to listen for NMR phenomena related to the pulse sequence. More specifically, the hybrid pulse sequence generator 110 includes a hybrid pulse sequence module 112 that stores information or parameters for one or more saturation pulses, an inversion pulse, and a detection sequence that make up each hybrid pulse sequence.

The hybrid pulse sequence generator 110 also includes a control module 114 that enables selection of or updates to hybrid pulse sequence options. For example, the time interval between the last saturation pulse and the inversion pulse may be selected or updated to increase or decrease sensitivity to fast-relaxing components. Further, the number of saturation pulses may be increased or decreased. Further, the detection sequence may be selected or switched between a free-induction decay (FID) pulse, a Carr-Purcell sequence, a Carr-Purcell-Meiboom-Gill (CPMG) sequence, or another sequence with different phase cycling schemes. It should be understood that the refocusing pulse or pulses in these sequences are not restricted to 180 degrees.

The NMR tool 100 also includes a measurement storage unit 116 to store NMR phenomena measurements related to the hybrid pulse sequence. The measurement storage unit 116 is accessible via wired or wireless data transmissions to provide the measurements to processing logic for analysis. For example, stored measurements may be used to derive $T_1$ distributions as described herein. In at least some embodiments, the measurements or values derived from the measurements may be displayed on a computer.

Figure 2:
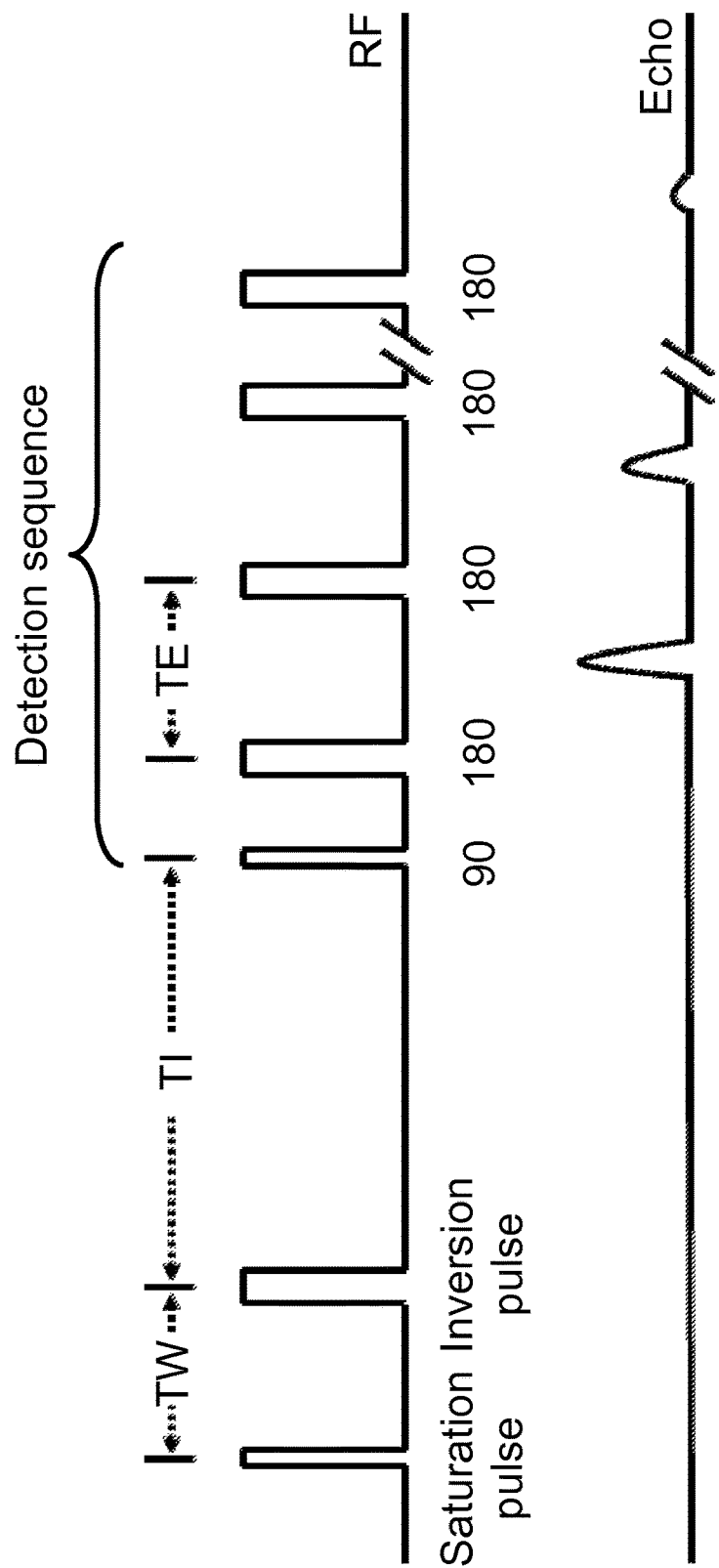
FIG. 2 shows an illustrative hybrid pulse sequence.

FIG. 2 shows an illustrative hybrid pulse sequence with a saturation pulse, an inversion pulse, and a detection sequence. Also, various time intervals are illustrated for the hybrid pulse sequence, including: a wait time (TW) between the saturation pulse and the inversion pulse; an inversion time interval (TI) between the inversion pulse and the detection sequence; and an interecho interval (TE) between pulses of the detection sequence. In operation, the saturation pulse places the target nuclei in an essentially demagnetized state. After TW in which the nuclei begin to repolarize parallel to the static field, the inversion pulse is applied to invert the (partial) polarization along the z-axis. After TI, measurements are secured using a standard CPMG sequence, in which a 90° pulse is followed by a sequence of 180° pulses spaced according to TE to generate echo signals (shown along the lower line in FIG. 2). The $T_1$ and $T_2$ measurements can be derived from the echo signal amplitudes in the usual way. In various embodiments, the time intervals can each be varied to improve measurement sensitivity and robustness. Further, through the use of gradients and frequency variation, the NMR measurements can further be spatially resolved.

Some variations to the hybrid pulse sequence of FIG. 2 can be envisioned. For example, for TI=0, the inversion pulse can be eliminated, but the resulting signals will be mathematically inverted. At longer values for TI, the inversion pulse can also be eliminated, resulting in a saturation-recovery pulse sequence. The time interval before the inversion pulse TW can be adjusted, or become variable, according to specific needs of the application. Further, the number of CPMG echoes acquired can change with TI, or a direct FID measurement can be acquired instead of a CPMG echo train when field homogeneity is sufficient. Further, a Carr-Purcell sequence, or another sequence with different phase cycling schemes may be used. Further, although the illustrated pulses in FIG. 2 have a square shape, other pulse shapes may be used. For example, a soft pulse or a fast passage involving frequency sweep would also work.

The disclosed hybrid pulse sequence for $T_1$ measurements is a combination of a saturation-recovery sequence and an inversion-recovery sequence. The saturation-recovery-CPMG method can be described symbolically as (sat)–TW–$\pi/2$–TE/2–($\pi$–TE/2–echo–TE/2)$_n$, where (sat) represents a saturation pulse or pulses, and $\pi$ and $\pi/2$ are RF pulses. Meanwhile, the inversion-recovery-CPMG method can be described symbolically as $\pi$–TI–$\pi/2$–TE/2–($\pi$–TE/2–echo–TE/2)$_n$.

Compared to the IR sequence, the SR sequence does not require a long time to reach full polarization between the measurements of two TWs. In contrast, the IR sequence requires a very long wait time (e.g., at least 3 times the longest $T_1$ component) to repolarize the magnetization. Therefore, from the logging speed consideration, the SR approach may be favored over IR.

The polarization buildup following the saturation pulse is described by $$M(TW) = M_0(1 - \exp(-TW/T_1)) \quad (1)$$

for a single $T_1$ component system. For a system containing a multiple component fluid fractions and/or pore sizes, the buildup can be described by $$M(TW) = \Sigma_{i=1}^{N} M_{0i}(1 - \exp(-TW/T_{1i})). \quad (2)$$

From Eqs. (1) and (2) is can be seen that the polarization build-up curve starts from near zero at low TW. On the other hand, using the IR sequence, the polarization evolution is described by $$M(TI) = M_0 \left[ 1 - 2\exp\left(-\frac{TI}{T_1}\right) \right] \quad (3)$$

for a single $T_1$ component system, and for a system containing multiple component fluid fractions and/or pore sizes, the buildup can be described by $$M(TI) = \sum_{i=1}^{N} M_{0i} \left[ 1 - 2\exp\left(-\frac{TI}{T_{1i}}\right) \right]. \quad (4)$$

The evolution of magnetization starts at nearly $-M_0$ at very low TI.

A distribution of $T_1$ may be obtained by inverting the evolution of the magnetization polarization curve with a multiexponential decay model described by Eq. (2) or (4). Because signals corresponding to different $T_{1i}$ should be greater than or equal to zero, a non-negative constraint is included in the inversion. The sensitivity of inversion to resolve the individual components depends, among others factors, on the signal-to-noise ratio (SNR) of the evolution of the polarization curve data. For the SR approach, the initial data points, corresponding to the short TWs, may have a very poor SNR; thus, the fast-relaxing components can suffer a greater error. On the other hand, for short TIs in the inversion-recovery sequence, the signal amplitude of the initial data points may be close to $M_0$ but opposite in the phase. Therefore, the SNR may be adequate.

The hybrid pulse sequence is advantageous in that it overcomes the long time required to run the IR sequence but maintains the advantage of this sequence's sensitivity to the fast decay $T_1$ components. The hybrid pulse sequence can be described as saturation-(partial-recovery)-inversion-recovery sequence (HSIR) and can be symbolically written as:

$$(\text{sat})-TW_i-\pi-TI_j-\pi/2-TE/2-(\pi-TE/2-\text{echo}-TE/2)_n. \quad (5)$$

The $TW_i$ can be fixed or variable but is usually a short time interval, which allows only the fastest relaxing component being fully polarized. The first saturation pulse establishes the well-defined state. After $TW_i$, $$M(TW_i)=M_0(1-\exp(-TW_i/T_1)) \quad (6a)$$

is the polarized magnitude of the magnetization. The following $\pi$ pulse inverts this $M(TW_i)$ signal to the $-z$ direction, and the remaining unpolarized magnetization, continues its course of building up the polarization. Subsequently, after the inversion-recovery with time $TI_j$, $$M = M_0 \cdot \left\{ \left(1 - e^{-\frac{TW_i}{T_1}}\right) \cdot \left(1 - 2e^{-\frac{TI_j}{T_1}}\right) + e^{\frac{TW_i}{T_1}} \cdot \left(1 - e^{-\frac{TI_j}{T_1}}\right) \right\} \quad (6b)$$

With algebraic simplification, Eq. (6a) can be rewritten as:

$$M = M_0 \cdot \left[1 - 2e^{-\frac{TI_j}{T_1}} + e^{-\frac{TI_j+TW_i}{T_1}}\right]. \quad (6c)$$

From this expression, it can be seen that if a TW value is sufficiently larger than a $T_1$ component value to be quantified, the third term in the bracket can be dropped, and TIs can be varied to estimate this component. Further, optimization of TW is possible as later described.

At the end of the CPMG echo train with n number of echoes, the magnetization is described by $$M = M_0 \cdot \left[1 - 2e^{-\frac{TI_j}{T_1}} + e^{-\frac{TI_j+TW_i}{T_1}}\right] \cdot e^{-\frac{nTE}{(T_1/R)}} \quad (7)$$

for a single relaxation time component system, where is used instead of explicitly. On the other hand, for a multiple-component system, $$M(TW_i) = \sum_{k=1}^{K} M_{0k} \cdot \left[1 - 2e^{-\frac{TI_j}{T_{1k}}} + e^{-\frac{TI_j+TW_i}{T_{1k}}}\right] \cdot e^{-\frac{nTE}{(T_{1k}/R_k)}}. \quad (8)$$

The disclosed hybrid pulse sequence preserves the time saving advantage of the saturation-recovery sequence while increasing the dynamic range and therefore the measurement accuracy of the fast relaxing components. The amplitude of the echoes in FIG. 2 is:

$$E_n = \Sigma_j M_j \{(1-e^{-TI/T_{1j}}) \cdot (1-2e^{-TR/T_{1j}}) + e^{-TI/T_{1j}} \cdot (1-e^{-TR/T_{1j}})\} \cdot e^{-n \cdot TE \cdot R_j/T_{1j}}, \quad (9)$$

where Mj is the equilibrium magnetization with a characteristic spin-lattice relaxation time $T_{1j}$, and Rj the $T_1/T_2$ ratio of that component. From Eq. 9 one can see that in the extreme case when TI=0, it is the same as the saturation-recovery case:

$$E_n = \Sigma_j M_j (1-e^{-TR/T_{1j}}) \cdot e^{-n \cdot TE \cdot R_j/T_{1j}}. \quad (10)$$

In another extreme case where TW is several times the longest $T_1$ component (thus consuming a lot more time), Eq. 9 reduces to:

$$E_n = \Sigma_j M_j (1-2e^{-TR/T_{1j}}) \cdot e^{-n \cdot TE \cdot R_j/T_{1j}}, \quad (11)$$

the same as that for IR. If, however, one chooses a TW (or several TWs) that is several times the $T_1$ of the fast relaxing components of the sample for smaller TI, and a TW of zero for larger TI, the accuracy enhancements in Eq. 11 are achieved for fast relaxing components without introducing too much overhead time compared to saturation-recovery (Eq. 10).

The performance of the hybrid pulse sequence is compared herein with SR and IR sequences. While the total porosity is straightforward to compare, the quantification of the fidelity of the $T_1$ distribution derived from the inversion of the $T_1$ evolutions of these sequences is more challenging. In the comparison, the Fréchet distance quantifies the resemblance between two $T_1$ distributions. More specifically, the Fréchet distance is calculated to compare the true (model) $T_1$ distribution and the $T_1$ distribution inverted from the magnetization evolutions from either the hybrid or SR sequence. As presented herein, the Fréchet distance is shorter for $T_1$ distributions derived from the hybrid sequence than those derived from the SR sequence.

To perform the comparison, random noise is added to the time-domain magnetization evolution data such that the noise reaches the typical levels found in either laboratory NMR core plug measurements or openhole logging data, respectively. Also, systems are modeled with different underlying $T_1/T_2$ ratio because the ability to resolve the relaxation time spectrum and quantify the fast relaxing components is $T_1/T_2$ ratio dependent. In each model, simulation is repeated at least 100 realizations with fresh random noises in the magnetization evolution data, and the conclusion is based on the statistical measures of the whole data set. From the simulations, improvements gained by using the hybrid pulse sequence are observable for both core and log-data noise level but are more significant in the high-level noise data, indicating that the sequence is indeed beneficial to the downhole logging environment. To objectively compare the capability of deriving petrophysical information from the two data acquisition methods, simulation of the magnetization evolutions with response to the same input models are generated with additive random noises at the level comparative to that typically found in core plug NMR measurements and NMR logging data.

The formation rock models used for the comparison are extracted from the observation of real NMR logging data in: (1) a North America shale gas well with dominant porosity in short-relaxation time range; (2) a heavy oil-bearing formation containing heavy oil and movable water; and (3) $T_2$ distributions of a carbonate reservoir having both micro- and macro-porosities. To add to the complexity of the model, a variable $R=T_1/T_2$ ratio is applied. The R values are set to be 3 for the shortest relaxation time component and 1 for the longest relaxation time component and progressively decrease from 3 to 1 for the intermediate components. Such a pattern of R variation is reasonable especially for heavy-oil and shale gas formations. The values of TWs and TIs in the hybrid sequence are listed in Table 1.

TABLE 1

The TW and TI times used in the hybrid sequence simulation

| TI | 0 | 0.5 | 1 | 2 | 3 | 4 | 8 | 16 | 40 | 100 | 300 | 500 | 1000 | 3000 |
|---|---|---|---|---|---|---|---|---|---|---|---|---|---|---|
| TW | 8 | 8 | 8 | 8 | 8 | 0 | 0 | 0 | 0 | 0 | 0 | 0 | 0 | 0 |

For the simulations, the interecho time of the echo trains following the hybrid and SR sequence is 0.3 ms and the number of echoes is 15. With these parameters, the difference in total data-acquisition time between this hybrid and the SR sequences is less than 1% (approximately equal). Note that the TW value is chosen to be zero for TI values greater than 4 ms, because it is no longer necessary for longer TIs and it saves time as well. For the SR sequence, the TW values are chosen to be the same as the TI values of the hybrid sequence listed in Table 1. Note that the plain IR sequence is not included in the comparison because it would take a very long time (the disadvantage is obvious).

Figure 3:
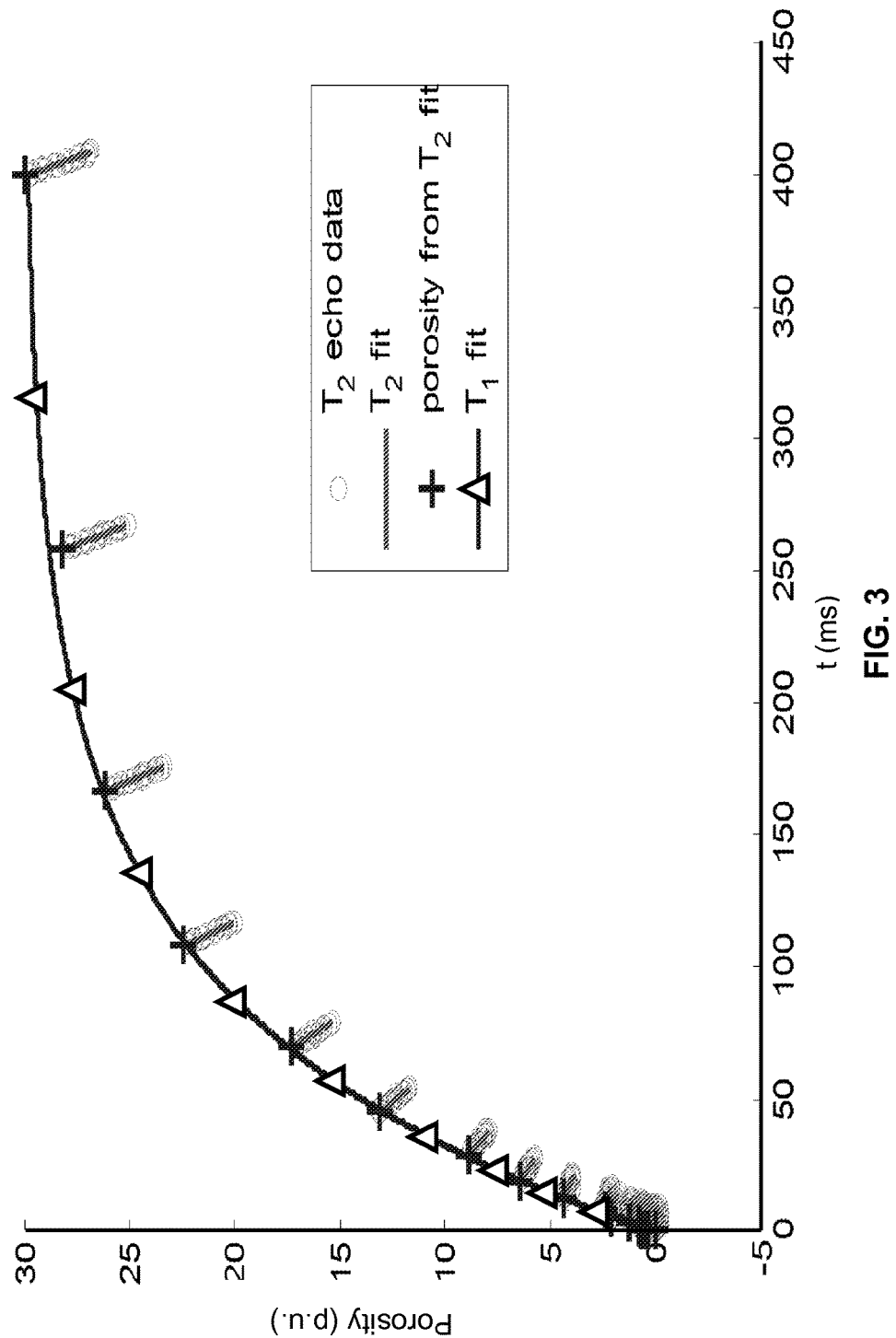
FIG. 3 shows an illustrative two-step inversion.

The simulation data is inverted in two steps. The first step inverts the echo trains with a multi-$T_2$ decay model to obtain the apparent porosity vector, $\phi(TW_i, TI_j)$. The second step inverts the $\phi(TW_i, TI_j)$ vector with a multi-$T_1$ polarization build-up model. The two-step inversion is illustrated in FIG. 3. The two-step inversion technique eliminates the need for estimating the unknown $T_1/T_2$ in the inversion process. The inversion processing algorithm included a regularization term where the normal regularization has been used for all data. The regularization coefficient is adjusted based on the signal strength and noise level.

For the quantitative comparison of the $T_1$ distributions from the inversion with the true $T_1$ relaxation-time distribution models, the Fréchet distances between the inversion results and the true models are calculated. The Fréchet distance is a measure of similarity between two curves that takes into account the location and ordering of the points along the curves. The shorter the Fréchet distance, the higher degree of similarity between the inversion result and the model $T_1$ distribution. In the comparison, the vertical scale of the partial porosity model is normalized to the same as the horizontal $\log(T_1)$ scale. The inversion results are normalized by the same factor. A discrete Fréchet distance computational algorithm can then be used to compute the distance. It can also be used for comparing core and log-derived relaxation time distributions. For the comparison, the curve misfit is computed as:

$$\sqrt{\Sigma_{i=1}^{nBins}(M_i^{inv}-M_i^{model})^2 / \#ofbins}. \quad (12)$$

Figures 4D, 4E, 4F:
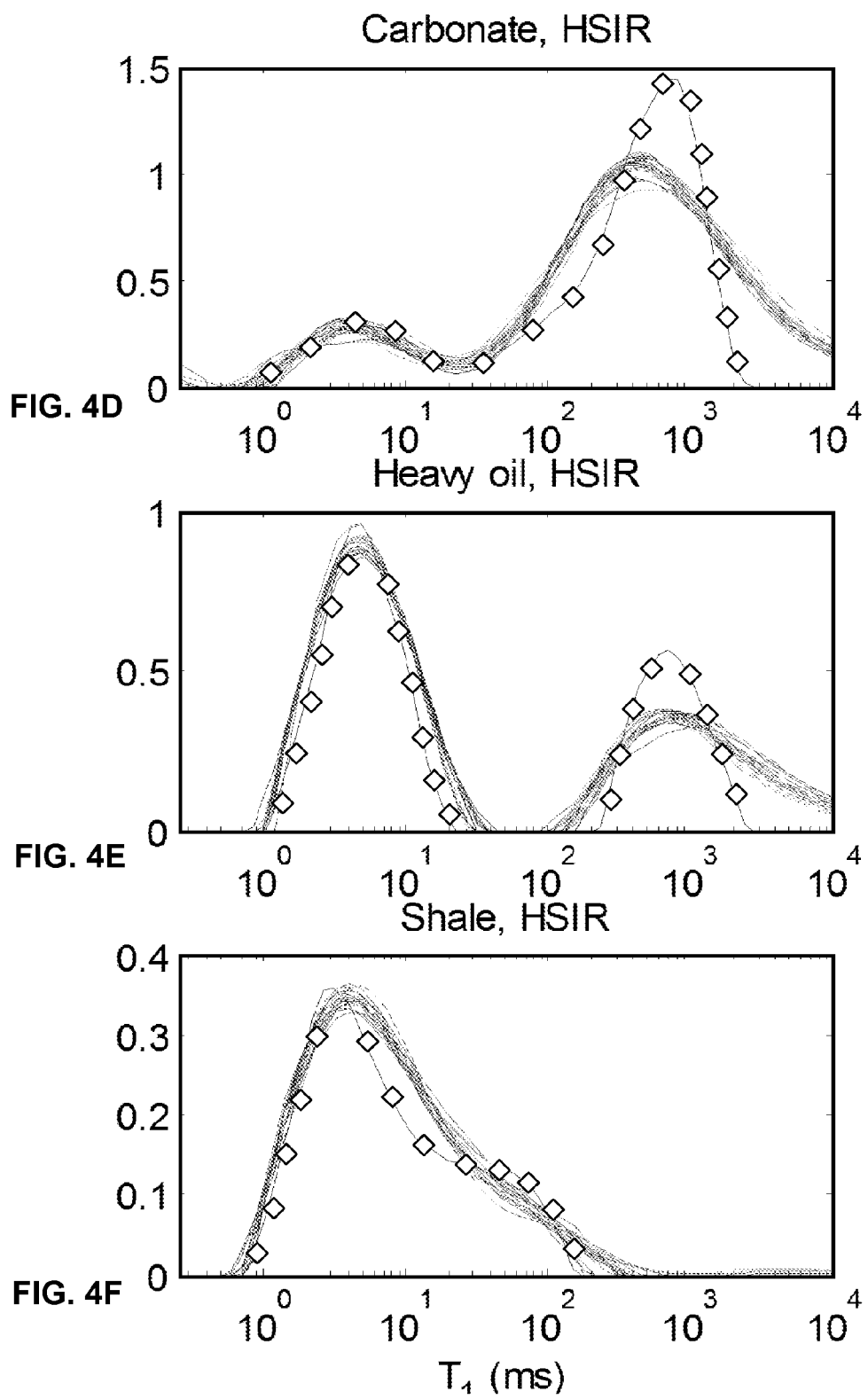
Figures 5A, 5B, 5C:
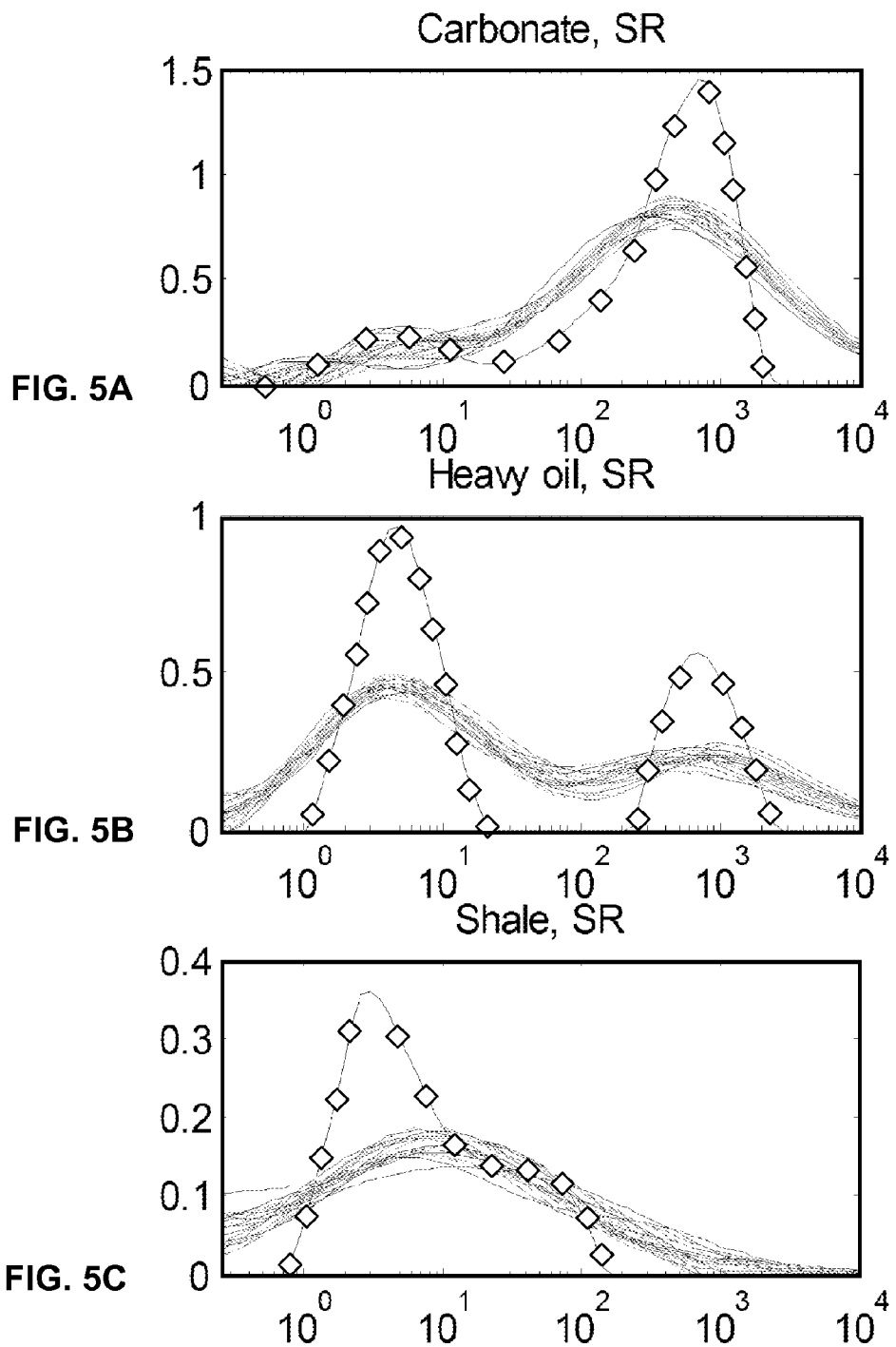
FIGS. 5A-5F show illustrative low signal-to-noise ratio (SNR) inversion results.
Figures 5D, 5E, 5F:
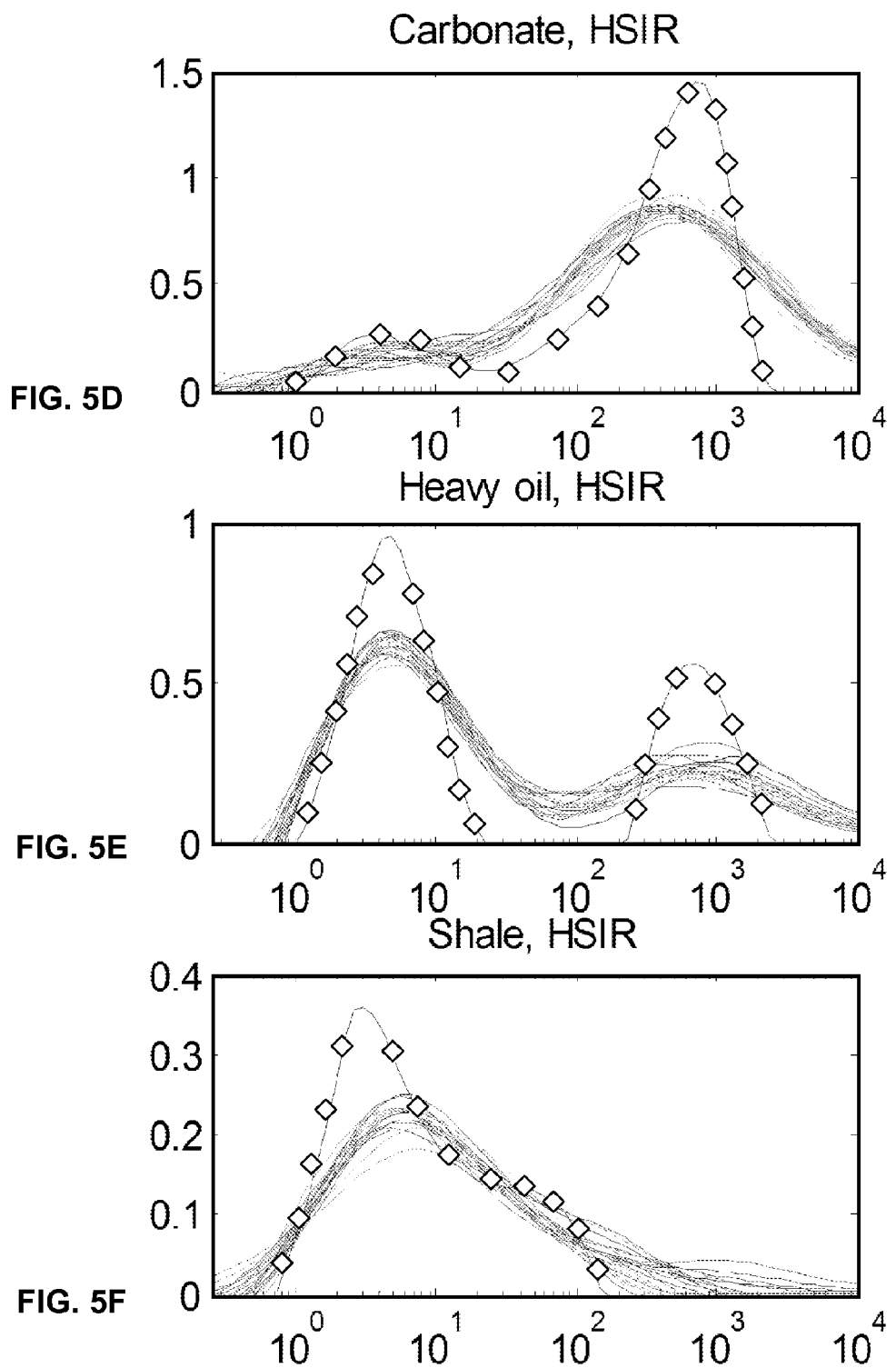

FIGS. 4A-4C show simulated inversion results using a saturation-recovery sequence. Similarly, FIGS. 4D-4F show simulated inversion results using a hybrid recovery sequence. In FIGS. 4A-4F, model $T_1$ distributions and multiple noise-realization of the inversion results are displayed for carbonate, heavy oil with movable water, and black shale formations. The total porosity of these simulations are 22 porosity units (p.u.) for carbonate, 15 p.u. for heavy oil, and 6 p.u. for gas shale, respectively. To perform the simulations of FIGS. 4A-4F, a fixed signal-to-noise ratio (SNR) of 200 is used, in the range for suitable laboratory core-plug NMR measurements.

In FIGS. 4A-4F, each model curve is represented as a line with diamonds, and the other lines are the inversion results. Using the naked eye, the high SNR data inversion results derived from both SR and the hybrid pulse sequence are observed to be quite good. For the heavy-oil and shale cases, the hybrid pulse sequence results recover the model distribution patterns more closely, particularly for the short relaxation-time ranges. This is consistent with the expectation that the hybrid pulse sequence has better sensitivity for the fast-relaxing components.

The Fréchet distances computed for the simulations of FIGS. 4A-4F compare the inversion results derived from these two sequences. The Fréchet distance and the misfit calculation values are shown in Table 2 indicating non-trivial improvements for hybrid pulse sequence data versus the SR pulse sequence data. The values listed in the table are the means of the values computed from the individual noise realizations.

TABLE 2

Statistical analysis of Fréchet Distance and Misfit for the cases shown in FIGS. 4A-4F

|  | Mean Fréchet Distance | STD of Fréchet Distance | Mean Misfit | STD of Misfit |
|---|---|---|---|---|
| Carbonate-SR | 2.75 | 0.23 | 0.2123 | 0.0103 |
| Carbonate-HSIR | 2.72 | 0.25 | 0.2100 | 0.0107 |
| Heavy Oil-SR | 2.22 | 0.19 | 0.1285 | 0.0080 |
| Heavy Oil-HSIR | 2.13 | 0.20 | 0.1097 | 0.0080 |
| Shale-SR | 1.30 | 0.19 | 0.0325 | 0.0032 |
| Shale-HSIR | 1.11 | 0.01 | 0.0291 | 0.0033 |

The more significant improvements are observed when the data have higher levels of noises. In logging operations, the noise level is determined by the formation, borehole environment, tool and acquisition configurations, and the data averaging. In the simulations, 0.5 p.u. of random noise is added to all the model data. For 22 p.u., 15 p.u., and 6-p.u. model formations, the corresponding SNR is 44, 30, and 12, respectively, and is in the typical range of logging data quality.

Compared to high SNR simulations shown in FIGS. 4A-4F, the improvements by using a hybrid pulse sequence are more significant for the low SNR simulations in FIGS. 5A-5F. The quantitative, statistical analysis of the Fréchet distance shows improvement for all simulations with more significant improvements achieved for heavy-oil and shale gas simulations. The less-significant improvement for carbonates with small amounts of microporosity is understandable because the weak-signal amplitudes at the short relaxation-time range, where the hybrid pulse sequence exhibits the advantage, do not contribute significantly to the Fréchet distance nor to the misfit. Nevertheless, for both the high SNR and low SNR simulations, hybrid pulse sequence results still consistently show an advantage. In other words, the consistency of the inversion results for hybrid pulse sequence data in the microporosity ranges for varying noise realizations is better than that for the SR data in the same region. The Fréchet distance and the misfit calculation values are shown in Table 3 indicating non-trivial improvements for hybrid pulse sequence data versus the SR pulse sequence data.

TABLE 3

Statistical analysis of Fréchet Distance and Misfit for the cases shown in FIGS. 5A-5F

|  | Mean Fréchet Distance | STD of Fréchet Distance | Mean Misfit | STD of Misfit |
| --- | --- | --- | --- | --- |
| Carbonate-SR | 4.07 | 0.23 | 0.2545 | 0.0105 |
| Carbonate-HSIR | 4.04 | 0.23 | 0.2508 | 0.0101 |
| Heavy Oil-SR | 5.03 | 0.29 | 0.2127 | 0.0105 |
| Heavy Oil-HSIR | 3.48 | 0.24 | 0.1688 | 0.0106 |
| Shale-SR | 5.20 | 0.35 | 0.0705 | 0.0056 |
| Shale-HSIR | 3.76 | 0.41 | 0.0513 | 0.0051 |

In FIGS. 5A-5F, each model curve is represented as a line with diamonds, and the other lines are the inversion results. Again, 0.5 p.u. of random noise is added to all the model data. For 22 p.u., 15 p.u., and 6-p.u. model formations, the corresponding SNR is 44, 30, and 12, respectively, and is in the typical range of logging data quality. The hybrid pulse sequence results recover the model distribution patterns more closely, and the improvements over SR results are more significant for the low SNR (poorer-quality) data of FIGS. 5A-5F than for the high-SNR data of FIGS. 4A-4F.

Figure 6:
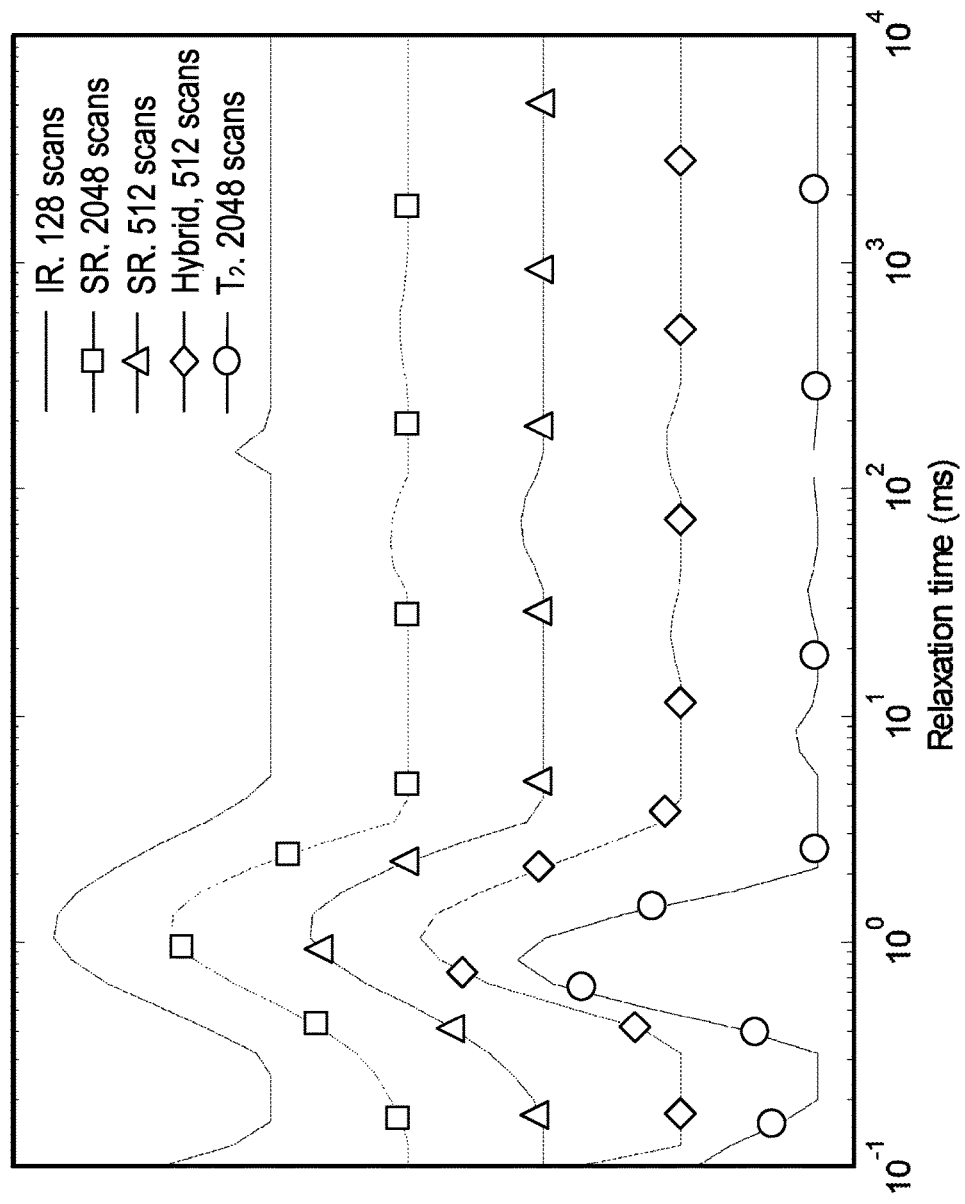
FIG. 6 shows a chart comparing illustrative relaxation times.

FIG. 6 compares the $T_1$ and $T_2$ inversion results from experimental data gathered with different NMR sequences using a North American shale plug saturated with water. One obvious difference between SR and hybrid pulse sequence $T_1$ measurements is that hybrid pulse sequence gives a very early $T_1$ component ($\leq 0.1$ ms) and a second peak centered at about 1 ms. The SR sequence, meanwhile, only gives one broader peak, albeit with some bias toward earlier components. Such a bias gets more pronounced with higher number of scans. However, even with 4 times more scans, SR sequence still cannot separate the two peaks. Such a peak separation should be "real", as confirmed by $T_2$ and the IR results shown also in FIG. 6. In shale, $T_1$ components $\leq 0.1$ ms should almost certainly come from organic matter. Therefore, the hybrid pulse sequence, just as the IR sequence, is more sensitive to earlier relaxation components and can even distinguish between the signal from organic matter and that from other materials. Advantageously, the hybrid pulse sequence can achieve this sensitivity at a fraction of the time used in IR measurements. For example, to obtain the result using 512 scans, it will take a little more than 1.5 hours for the hybrid sequence, but more than 16 hours for the IR sequence if one uses 3 seconds as the wait time.

Figure 7B:
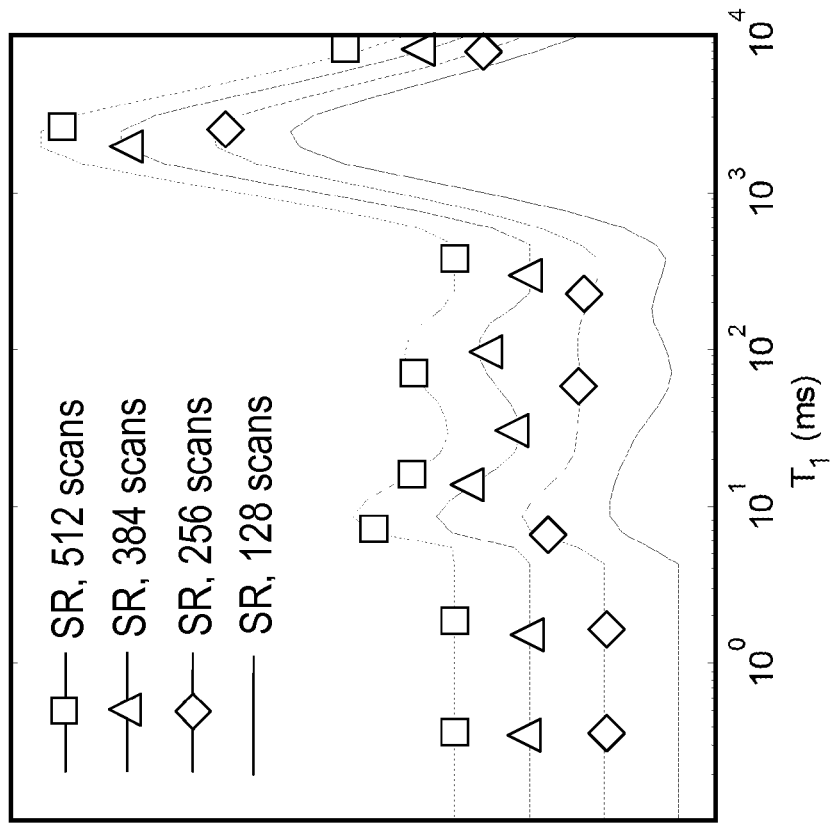
FIGS. 7A and 7B show illustrative charts comparing $T_1$ inversion results using a hybrid pulse sequence and a saturation-recovery pulse sequence.
Figure 7A:
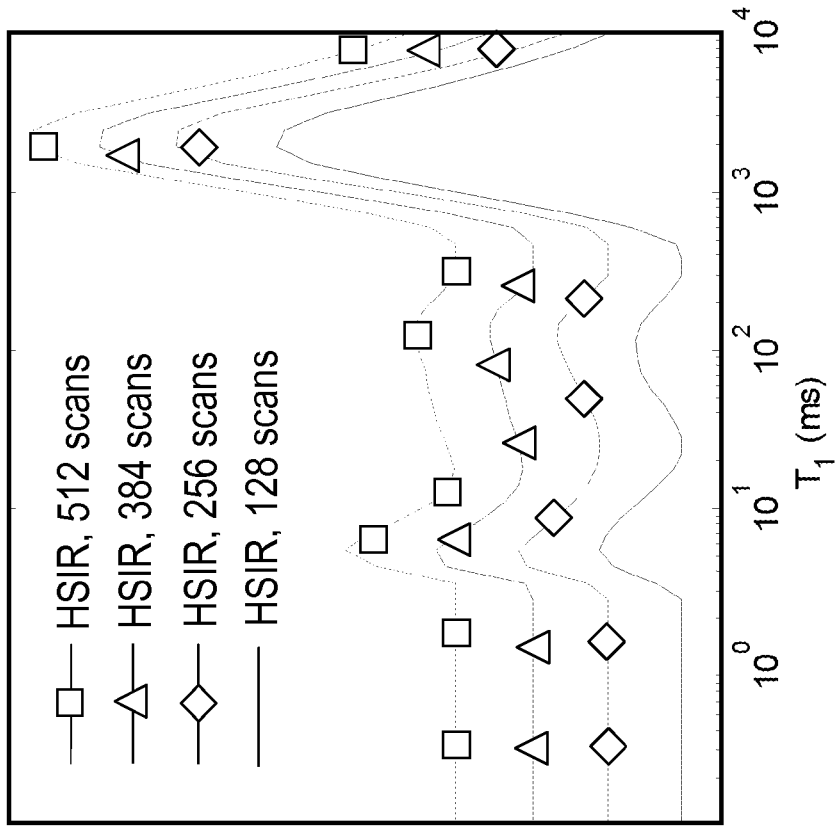

FIGS. 7A and 7B shows the comparison of $T_1$ distributions from a North American carbonate plug using hybrid pulse and SR sequences, respectively, with various numbers of scans. The carbonate sample has a lot of vugs, as manifested by the large peak at more than 1 second relaxation times. At the same time, the sample has a certain degree of microporosity and meso-porosity, as indicated by the earlier peaks in the $T_1$ distribution pattern. It can be seen that at 128 scans, the hybrid pulse sequence separates the earlier two peaks very well, with correct amplitudes. In comparison, with SR, 384 scans are needed to have a good separation. For the hybrid pulse sequence, at higher number of scans, more features appears for the second peak, while these features are absent in SR results. All of these observations suggest that the hybrid pulse sequence is indeed more sensitive to earlier components of $T_1$ distribution and offers a better characterization at minimal time cost if these components do exist in the sample. Compared to IR, the hybrid pulse sequence has a significant advantage because for IR, each scan needs an additional delay of more than 15 seconds to completely relax the nuclear spins, and each $T_1$ measurement includes 40 wait times. As an example, the time saving for a 128-scan experiment would be more than 128*15*40 seconds=21.3 hours.

Figure 8A:
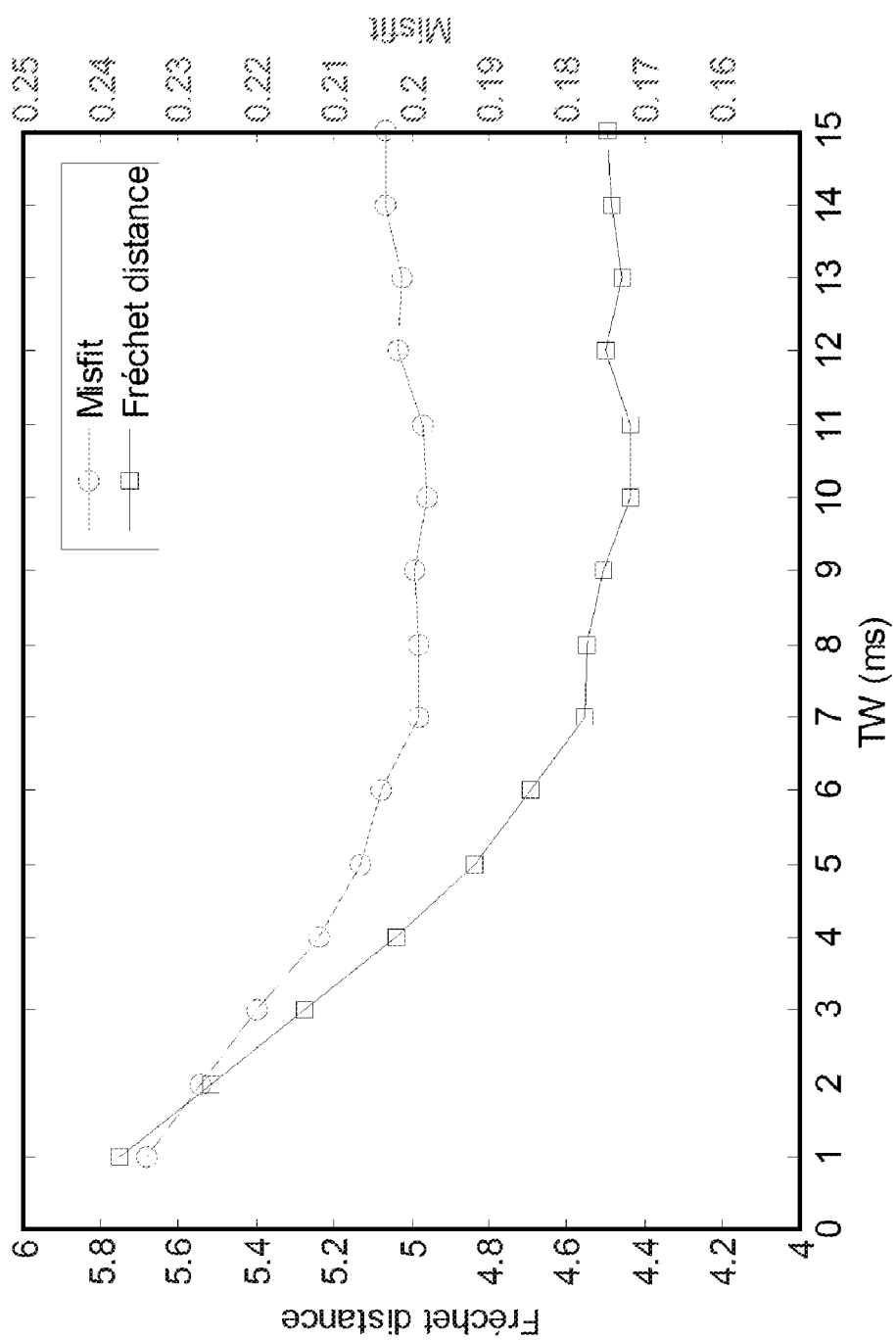
FIG. 8A shows a chart with illustrative wait time (TW) information related to use of a hybrid pulse sequence in a heavy-oil environment.
Figure 8B:
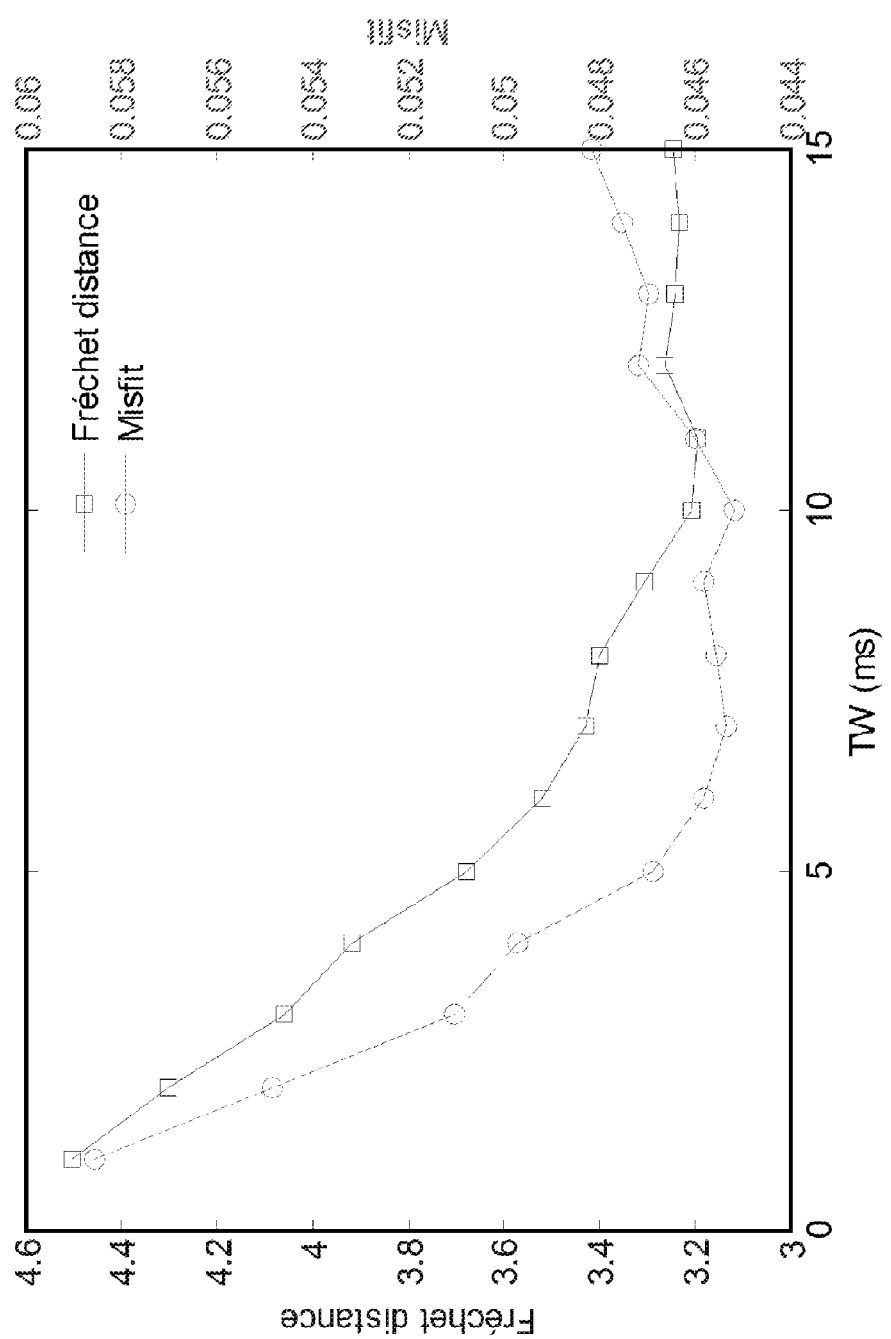
FIG. 8B shows a chart with illustrative TW information related to use of a hybrid pulse sequence in a shale-oil environment.

From Eq. (8), it can be recognized that the advantage of using the hybrid pulse sequence over the SR sequence is dependent on the selection of the TW and TI values, as well as the $T_1$ distribution of the sample being investigated. In some embodiments, simulations may be performed to determine an optimal TW value. Such simulations may be performed to test heavy-oil and shale gas models with different TW values. Subsequently, the corresponding Fréchet distance and the curve misfit values are computed. Without limitation, the simulation SNR is maintained at 20. FIGS. 8A and 8B show two example simulation results for heavy-oil and shale gas, respectively.

For both simulations, the minimum Fréchet distance and misfit consistently reside at approximately 10 ms. The fact that the optimal TW does not vary significantly from one formation scenario to another is helpful in implementing the hybrid pulse sequence in a logging data-acquisition scheme. Because pore sizes and fluid saturations inevitably vary from depth to depth, and the variations are not predictable before logging operations, it is desirable to use one set of parameters to log an entire well.

Figure 9:
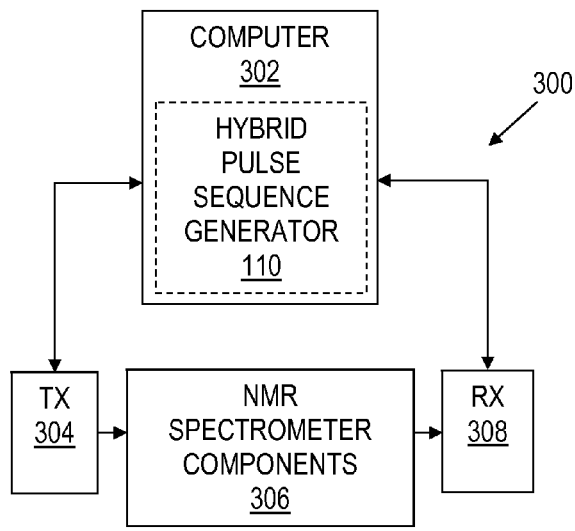
FIG. 9 shows an illustrative NMR system.

FIG. 9 shows a block diagram of an illustrative NMR system 300. The NMR logging system 300 includes a computer 302 that, in at least some embodiments, directs the operations of hybrid pulse sequence generator 110. In such embodiments, the computer stores and executes instructions to enable NMR logging based on a hybrid pulse sequence as described herein. The computer 302 is configured to provide commands, programming, and/or data to a transmitter 304. The transmitter 304 may include a programmable pulse sequence device or storage, a radio frequency (RF) synthesizer, a phase shifter, a pulse gate, an amplifier, and/or other components to control the pulsed magnetic field for NMR logging operations including the hybrid pulse sequence operations described herein. In different embodiments, the hybrid pulse sequence generator 110 enables adjustment of hybrid pulse sequence options based on a default configuration, user selection, and/or calibration. For example, the time interval (TW) between the last saturation pulse and the inversion pulse may be selected or updated to increase or decrease sensitivity to fast-relaxing components. Further, the number of saturation pulses may be increased or decreased. Further, the detection sequence may be selected or switched between an FID pulse, a Carr-Purcell sequence, a CPMG sequence, or another sequence with different phase cycling schemes. In short, the transmitter 304 is configured to output any of the hybrid pulse sequence variations described herein.

The NMR logging system 300 also includes NMR spectrometer components 306 used for NMR logging operations. Examples of NMR spectrometer components 306 include one or more magnets, shim coils, probes/antennas, and/or field-frequency lock components. Further, the NMR spectrometer components 306 may include a duplexer that enables separation between transmission current and reception current. The receiver 308 of NMR logging system 300 is configured to receive and decode NMR signals. The receiver 310 may include an analog-to-digital converter (ADC), filters, mixers, splitters, pre-amplifiers, and/or other components to receive NMR signals and recover measurement data. In accordance with embodiments, receiver 310 is configured to recover free-induction decay or spin echo data using available receiver window options. The recovered measurement data is output from the receiver 308 to computer 310 for storage and analysis. Thus, the computer 302 may communicate with the transmitter 304 and the receiver 308 of system 300 to enable NMR logging operations in which a hybrid pulse sequence is used to recover spin echo data and/or free-induction decay data.

Figure 10:
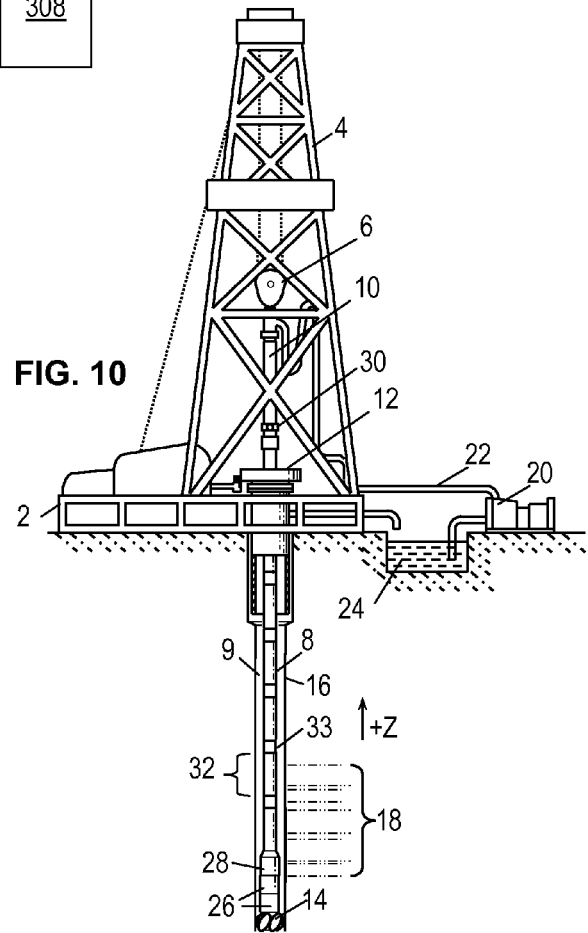
FIG. 10 shows an illustrative logging while drilling (LWD) environment.

FIG. 10 shows an illustrative logging while drilling (LWD) environment, which serves as an exemplary usage context for the NMR tool 100 or NMR system 300 described herein. A drilling platform 2 supports a derrick 4 having a traveling block 6 for raising and lowering a drill string 8. A drill string kelly 10 supports the rest of the drill string 8 as it is lowered through a rotary table 12. The rotary table 12 rotates the drill string 8, thereby turning a drill bit 14. As bit 14 rotates, it creates a borehole 16 that passes through various formations 18. A pump 20 circulates drilling fluid through a feed pipe 22 to kelly 10, downhole through the interior of drill string 8, through orifices in drill bit 14, back to the surface via the annulus 9 around drill string 8, and into a retention pit 24. The drilling fluid transports cuttings from the borehole 16 into the pit 24 and aids in maintaining the integrity of the borehole.

The drill bit 14 is just one piece of an open-hole LWD assembly that includes one or more drill collars 26 and logging tools 28, 32. Drill collars 26 are thick-walled steel pipe sections that provide weight and rigidity for the drilling process. The logging tools 28, 32 (some of which may be built in to the drill collars) gather measurements of various drilling or formation parameters. Either of logging tools 28, 32 may include an NMR logging tool configured to perform and/or be directed by the calibration techniques described herein. Measurements from the logging tools 28, 32 can be acquired by a telemetry sub (e.g., built in to logging tool 28) to be stored in internal memory and/or communicated to the surface via a communications link. Mud pulse telemetry is one common technique for providing a communications link for transferring logging measurements to a surface receiver 30 and for receiving commands from the surface, but other telemetry techniques can also be used.

Figure 11:
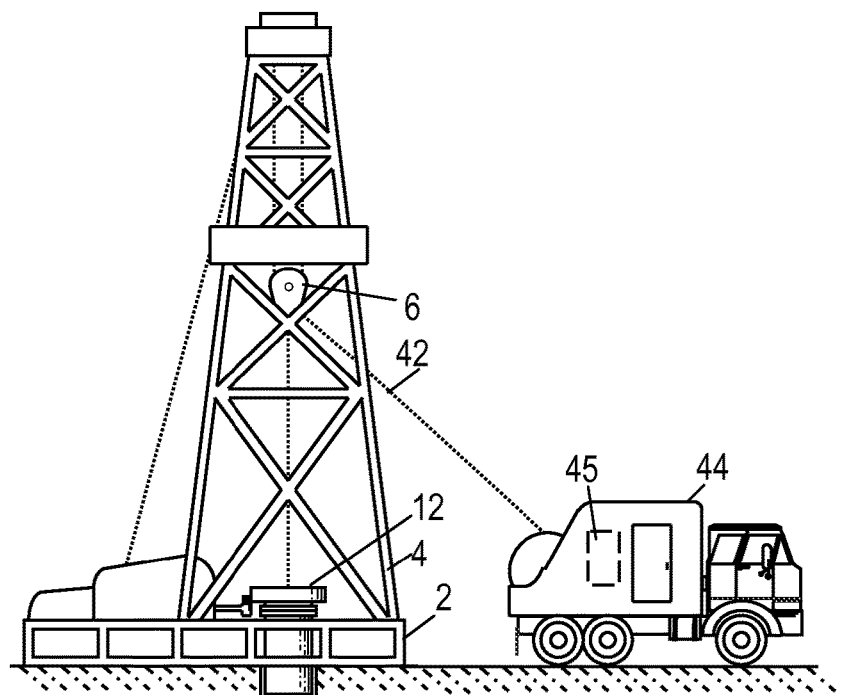
FIG. 11 shows an illustrative wireline logging environment.

At various times during the drilling process, the drill string 8 may be removed from the borehole 16 as shown in FIG. 11. Once the drill string 8 has been removed, logging operations can be conducted using a wireline logging string 34 (i.e., an assembly of wireline logging tools suspended by a cable 42 having conductors for transporting power to the tools and telemetry from the tools to the surface). It should be noted that various types of formation property sensors can be included with the wireline logging sonde 34. For example, the illustrative wireline logging sonde 34 includes logging tool 32, which may correspond to an NMR logging tool configured to perform and/or be directed by the hybrid pulse sequence techniques described herein. The logging tool 32 may be coupled to other modules of wireline logging sonde 34 by one or more adaptors 33.

A wireline logging facility 44 collects measurements from the logging tool 32, and includes computing facilities 45 for managing logging operations, acquiring and storing the measurements gathered by the wireline logging sonde 34, and optionally processing the measurements for display to a user. For the logging environments of FIGS. 10 and 11, measured parameters can be recorded and displayed in the form of a log, i.e., a two-dimensional graph showing the measured parameter as a function of tool position or depth.

Figure 12:
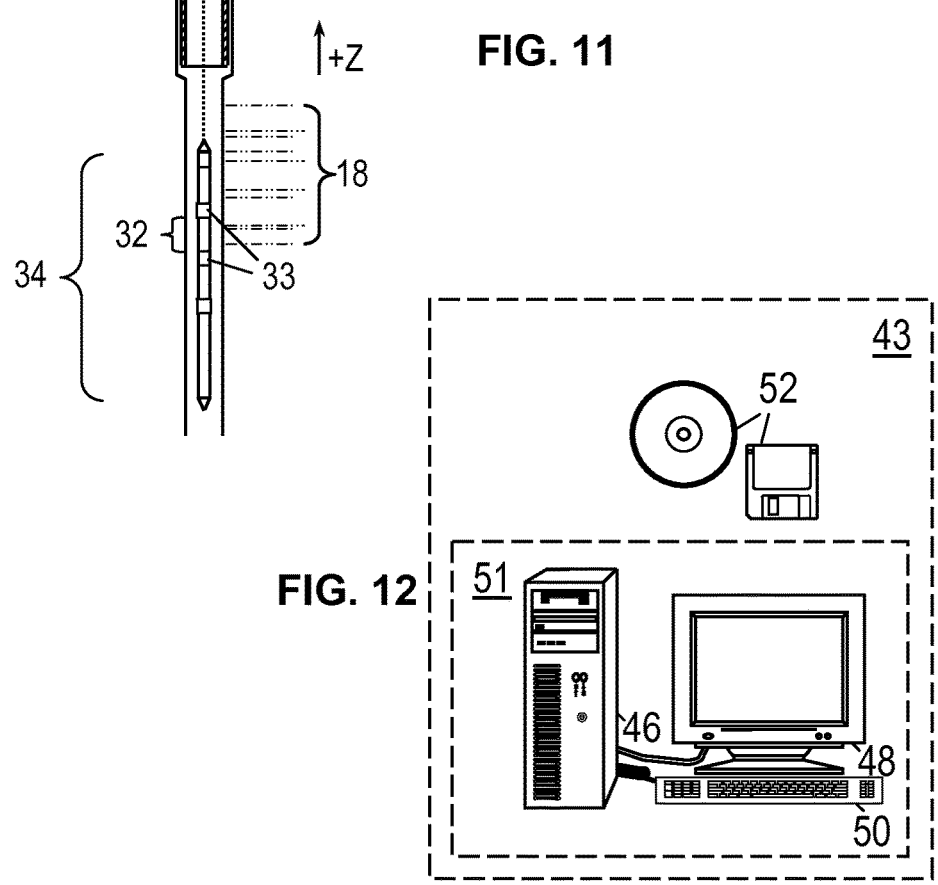
FIG. 12 shows an illustrative computer system for managing logging operations.

FIG. 12 shows an illustrative computer system 43 for managing logging operations. The computer system 43 may correspond to, e.g., an onsite logging facility for the drilling rig of FIG. 10, the computing facilities 45 of the wireline logging facility 44 of FIG. 11, or a remote computing system that manages logging operations. The computer system 43 may include wired or wireless communication interfaces for directing logging operations and/or receiving logging measurements. As shown, the illustrative computer system 43 includes user workstation 51 with a computer chassis 46 coupled to a display device 48 and a user input device 50. The computer chassis 46 includes one or more information storage devices for accessing software (shown in FIG. 12 in the form of removable, non-transitory information storage media 52) that configures the computer system to interact with a user, enabling the user to process the logging data and, in the case of local logging facilities, to manage logging operations including analyzing borehole conditions. The software may also be downloadable software accessed through a network (e.g., via the Internet). In some embodiments, illustrative computer system 43 executes software that performs the hybrid pulse sequence techniques described herein and/or directs logging operations of a NMR logging tool (e.g., NMR logging tool 100 or 32) using the disclosed hybrid pulse sequence techniques.

In some embodiments, the computer system 43 includes a non-transitory computer readable medium with a hybrid pulse sequence software tool. The software tool, when executed, causes a processor of the computer system 43 to provide a hybrid pulse sequence or suitable parameters from which a hybrid pulse sequence may be generated.

Figure 13:
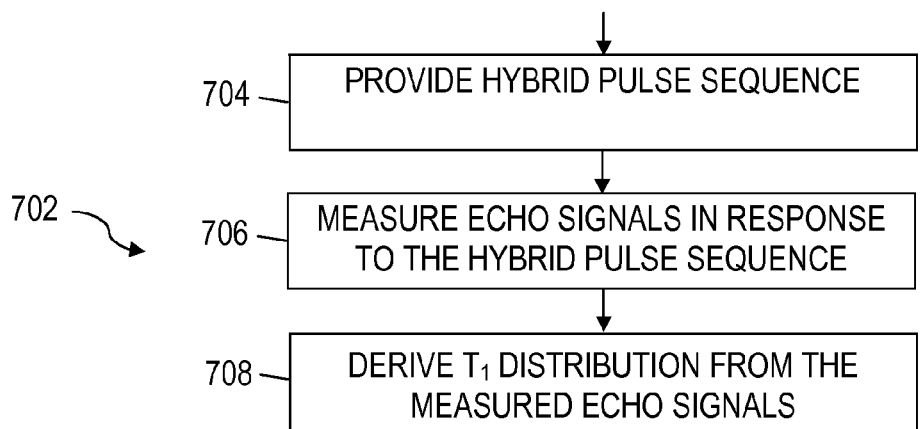
FIGS. 13 and 14 are flowcharts of illustrative NMR methods.

FIG. 13 is a flowchart of an illustrative NMR method 702. The NMR method 702 may be performed, for example, by a downhole wireline logging tool, a LWD tool, or a laboratory tool. In method 702, a hybrid pulse sequence in provided at block 704. The hybrid pulse sequence may correspond to any of the hybrid pulse sequence variations described herein. The provided hybrid pulse sequence may include, for example, a saturation pulse, an inversion pulse, and a detection sequence. The detection sequence may correspond to an FID sequence, a Carr-Purcell sequence, a CPMG sequence, or another sequence with different phase cycling schemes. In some embodiments, the hybrid pulse sequence includes multiple saturation pulses. At block 706, echo signals are measured in response to the hybrid pulse sequence provided at block 704. At block 708, a $T_1$ distribution is derived from the measured echo signals. The derived $T_1$ distribution may be displayed to a user using a computer. Additionally or alternatively, a formation property may be displayed as a function of tool position based on the derived $T_1$ distribution.

In some embodiments, the NMR method 702 includes additional steps. For example, the NMR method 702 may include selecting a time interval between the saturation pulse and the inversion pulse. The selection criteria may be based on user-input, predetermined measurement criteria, or other factors. In some embodiments, the NMR method 702 may include adjusting a time interval between the saturation pulse and the inversion pulse from a first value to a second value that is different than the first value.

Figure 14:
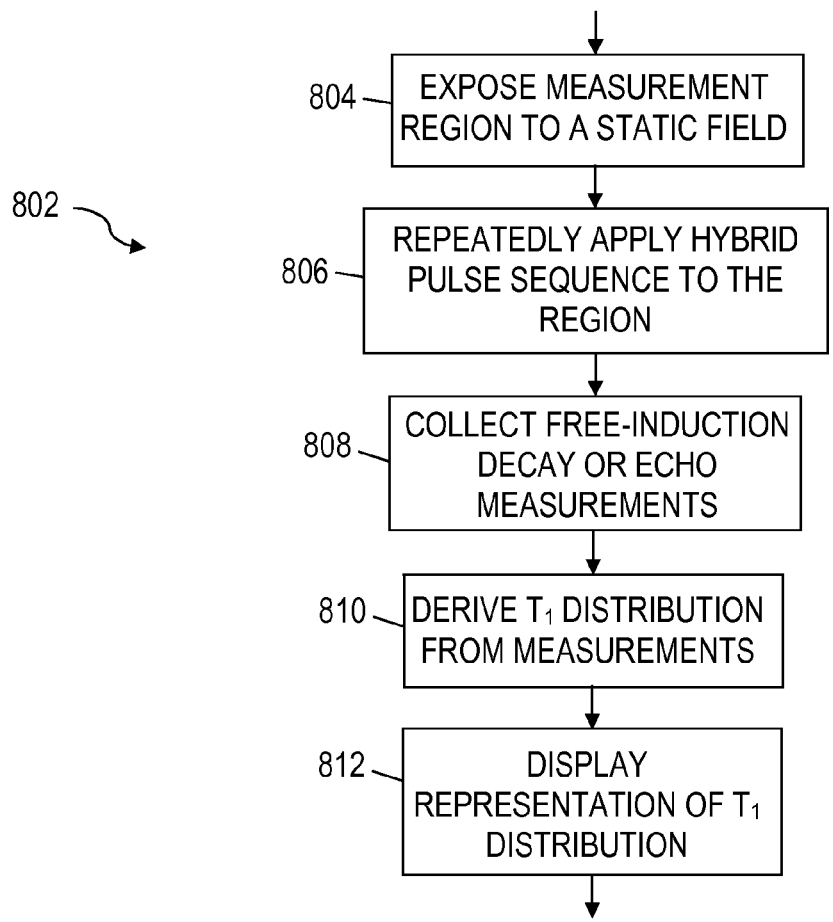

FIG. 14 is a flowchart of another illustrative NMR method 802. Again, the NMR method 802 may be performed, for example, by a downhole wireline logging tool, a LWD tool, or a laboratory tool. In method 802, a measurement region is exposed to a static magnetic field at block 804. At block 806, a hybrid pulse sequence is repeatedly applied to the measurement region. In at least some embodiments, the hybrid pulse sequence includes, in order: a saturation pulse, an inversion pulse, a 90° pulse, and optionally one or more 180° pulses to induce echo signals. Measurements, corresponding to the hybrid pulse sequence, are collected at block 808. The collected measurements may correspond to a free-induction decay signal caused by the 90° pulse or to echo signal caused by one or more 180° pulses. A $T_1$ distribution is derived from the collected measurements at block 810. Finally, a representation of the $T_1$ distribution is displayed at block 812.

In some embodiments, the NMR method 802 includes additional steps. For example, the NMR method 802 may include varying a time interval (TW) between the inversion pulse and the 90° pulse between repeated applications of the hybrid pulse sequence. Further, the NMR method 802 may include spacing the varying TW equally on a logarithmic scale. Further, the NMR method 802 may include spacing, on a logarithmic scale, the varying TW more closely for lower values than for higher values.

Numerous other modifications, equivalents, and alternatives, will become apparent to those skilled in the art once the above disclosure is fully appreciated. It is intended that the following claims be interpreted to embrace all such modifications, equivalents, and alternatives where applicable.

What is claimed is:

1. A nuclear magnetic resonance (NMR) method that comprises:
   repeatedly applying, to a formation sample, a hybrid pulse sequence having a saturation pulse, an inversion pulse, and a detection sequence;
   selecting a time interval between the saturation pulse and the inversion pulse during the repeated application of the hybrid pulse sequence to increase sensitivity to fast-relaxing components in the formation sample, wherein the time interval is determined based, at least in part, on a $T_1$ value associated with the fast-relaxing components in the formation sample;
   measuring echo signals in response to the repeated application of the hybrid pulse sequence; and
   deriving a $T_1$ distribution from the measured echo signals.

2. The NMR method of claim 1, further comprising displaying a representation of the $T_1$ distribution.

3. The NMR method of claim 1, wherein the hybrid pulse sequence comprises multiple saturation pulses.

4. The NMR method of claim 1, wherein the detection sequence comprises a free-induction decay (FID) pulse.

5. The NMR method of claim 1, wherein the detection sequence comprises a spin-echo sequence, a Carr-Purcell sequence, a Carr-Purcell-Meiboom-Gill (CPMG) sequence, or a sequence with different phase cycling schemes.

6. The NMR method of claim 1, further comprising adjusting a time interval between the saturation pulse and the inversion pulse from a first value to a second value that is different than the first value during the repeated application of the hybrid pulse sequence to increase sensitivity to said fast-relaxing components.

7. The NMR method of claim 1, wherein said repeated application of the hybrid pulse sequence is performed by a downhole NMR logging tool or logging-while-drilling (LWD) NMR tool.

8. The NMR method claim 1, wherein said repeated application of the hybrid pulse sequence is performed by a laboratory NMR tool.

9. The NMR method of claim 1, wherein the $T_1$ value of the fast-relaxing components comprises a value below 10 ms.

10. The method of claim 1, further comprising:
    performing one or more simulations, wherein results of the simulation are utilized in determining the $T_1$ value associated with the fast-relaxing components.

11. A nuclear magnetic resonance (NMR) system, comprising:
    a hybrid pulse sequence module to apply a hybrid pulse sequence with a saturation pulse, an inversion pulse, and a detection sequence; and
    a control module to select a time interval between the saturation pulse and the inversion pulse during repeated application of the hybrid pulse sequence to a formation sample to increase sensitivity to fast-relaxing components in the formation sample, wherein the time interval is determined based, at least in part, on a $T_1$ value associated with the fast-relaxing components in the formation sample.

12. The NMR system of claim 11, wherein the hybrid pulse sequence module and the control module correspond to software modules stored in computer-readable memory and executable by a processor.

13. The NMR system of claim 11, wherein the hybrid pulse sequence module and the control module correspond to hardware modules.

14. The NMR system of claim 11, further comprising:
    a static magnetic field source;
    a pulsed magnetic field source; and
    a measurement storage unit to store spin-lattice time constant ($T_1$) distribution measurements based on the repeated application of the hybrid pulse sequence.

15. The NMR system of claim 11, wherein the NMR system is part of a downhole logging tool or logging-while-drilling (LWD) tool.

16. The NMR system of claim 11, wherein the NMR system is part of a laboratory tool.

17. The NMR system of claim 11, wherein the $T_1$ value of the fast-relaxing components comprises a value below 10 ms.

18. The NMR system of claim 11, wherein the $T_1$ value associated with the fast-relaxing components is determined according to one or more simulations.

19. A nuclear magnetic resonance (NMR) data acquisition method that comprises:
- exposing a measurement region of a formation sample to a static field;
- repeatedly applying a pulse sequence to the measurement region, the pulse sequence including, in order: a saturation pulse, an inversion pulse, a 90° pulse, and optionally one or more 180° pulses to induce echo signals, wherein a time interval between the inversion pulse and the 90° pulse varies for repeated applications of the pulse sequence to increase sensitivity to fast-relaxing components in the formation sample, wherein values for the time interval are spaced on a logarithmic scale;
- collecting measurements of a free-induction decay signal caused by the 90° pulse or measurements of the echo signals;
- deriving a measurement of a $T_1$ distribution from said measurements; and
- displaying to a user a representation of the $T_1$ distribution.

20. The method of claim 19, wherein values for the time interval are equally spaced on the logarithmic scale.

21. The method of claim 19, wherein, the values for the time interval are more closely spaced for lower values than for higher values.

22. The method of claim 19, wherein the fast-relaxing components have a $T_1$ value below 10 ms.

\* \* \* \* \*